United States Patent [19]

Matsuo et al.

[11] 4,385,186
[45] May 24, 1983

[54] OPTICALLY ACTIVE 4-HYDROXY-3-METHYL-2-(2-PROPYNYL)-2-CYCLOPENTENONE

[75] Inventors: Noritada Matsuo, Itami; Kazunori Tsushima, Nishinomiya, both of Japan

[73] Assignee: Sumitomo Chemical Company, Limited, Osaka, Japan

[21] Appl. No.: 160,617

[22] Filed: Jun. 18, 1980

[30] Foreign Application Priority Data

Jun. 21, 1979 [JP] Japan ................................. 54/78873

[51] Int. Cl.³ ........................................... C07C 49/537
[52] U.S. Cl. ................................... 568/379; 424/306;
560/84; 560/124; 568/346; 568/356
[58] Field of Search ........................ 568/346, 379, 356

[56] References Cited

U.S. PATENT DOCUMENTS 3,931,291  1/1976  Horiuchi .......................... 568/346 X
4,206,151  6/1980  Grudzinskas ..................... 568/379 X
4,217,251  8/1980  Dastur ............................. 568/379 X

*Primary Examiner*—Natalie Trousof
*Assistant Examiner*—Vera C. Clarke
*Attorney, Agent, or Firm*—Stevens, Davis, Miller & Mosher

[57] ABSTRACT

The present invention relates to a method for producing an optically active (+)-(s)-4-hydroxy-3-methyl-2-2'-propynyl-2-cyclopentenone which comprises reacting (±)-4-hydroxy-3-methyl-2-2'-propynyl-2-cyclopentenone acid phthalate of the formula (II),

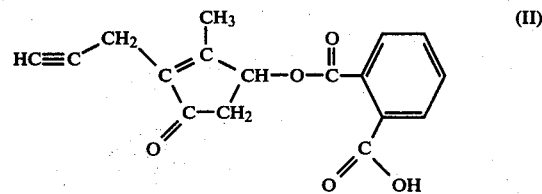

with an optically active (+)-α-phenyl-β-p-tolylethylamine to produce diastereomer salts, separating an optically active (−)-4-hydroxy-3-methyl-2-2'-propynyl-2-cyclopentenone acid phthalate by making use of a solubility difference between the diastereomer salts, and then hydrolyzing said optically active acid phthalate in water or a solvent containing water in the presence or absence of a base below the small excess of the stoichiometric amount, and novel (±)-4-hydroxy-3-methyl-2-2'-propynyl-2-cyclopentenone acid phthalate and its production.

1 Claim, No Drawings

OPTICALLY ACTIVE 4-HYDROXY-3-METHYL-2-(2-PROPYNYL)-2-CYCLOPENTENONE

The present invention relates to a method for producing an optically active (+)-(s)-4-hydroxy-3-methyl-2-2'-propynyl-2-cyclopentenone of the formula (I),

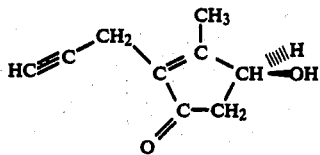

More particularly, it relates to a method for producing an optically active (+)-(s)-4-hydroxy-3-methyl-2-2'-propynyl-2-cyclopentenone of the formula (I) which comprises reacting (±)-4-hydroxy-3-methyl-2-2'-propynyl-2-cyclopentenone acid phthalate of the formula (II),

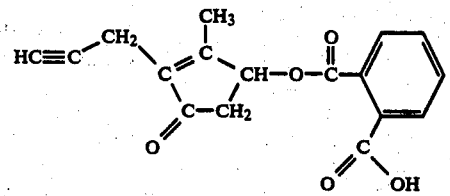

with an optically active (+)-α-phenyl-β-p-tolylethylamine to produce diastereomer salts, separating an optically active (−)-4-hydroxy-3-methyl-2-2'-propynyl-2-cyclopentenone acid phthalate by making use of a solubility difference between the diastereomer salts, and then hydrolyzing said optically active acid phthalate in water or a solvent containing water in the presence or absence of a base below the small excess of the stoichiometric amount.

Further, the present invention relates to novel (±)-4-hydroxy-3-methyl-2-2'-propynyl-2-cyclopentenone acid phthalate of the formula (II) and its production. More particularly, it relates to a method for producing (±)-4-hydroxy-3-methyl-2-2'-propynyl-2-cyclopentenone acid phthalate of the formula (II) which comprises reacting (±)-4-hydroxy-3-methyl-2-2'-propynyl-2-cyclopentenone with phthalic acid in the presence of a base.

Allethrin of the formula (III),

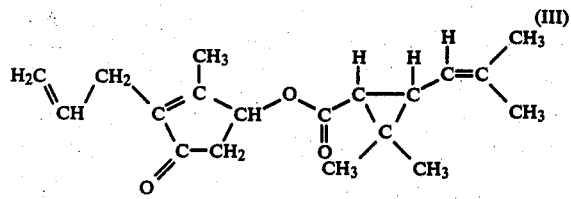

known as typical agricultural chemicals having the skeleton of cyclopentenolone was invented by M. S. Schechter in 1949, and it has widely been used in the world because of its excellent insecticidal activity and low toxicity. As to a method for synthesizing the alcohol moiety of allethrin, i.e. allethrolone of the formula (IV),

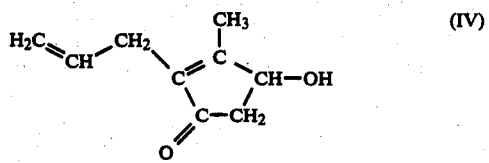

there are many well-known ones including synthetic methods for the optical isomers of allethrolone.

While it is well known that esters resulting from cyclopentenolone of the formula (I) having a similar structure to allethrolone and various acids have also a strong insecticidal activity like allethrin, and particularly that the compound of the formula (V),

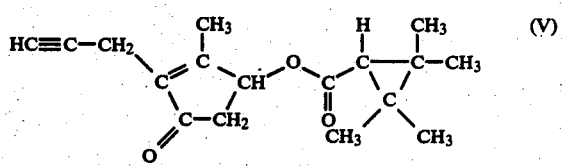

which is an ester resulting from cyclopentenolone and 2,2,3,3-tetramethylcyclopropanecarboxylic acid, has extremely strong knock-down and lethal effects (Published Examined Japanese Patent Application No. 15843/1975).

Further, the alcohol of the formula (I) has an asymmetric carbon atom at the 4-position so that it exists as two optical isomers. And, an ester resulting from one of the isomers, an optically active (+)-(s)-4-hydroxy-3-methyl-2-2'-propynyl-2-cyclopentenone, and 2,2,3,3-tetramethylcyclopropanecarboxylic acid, has an insecticidal activity of about 2 times as strong as that of its racemate.

As a result of the inventors' extensive study over a long period of time, the inventors succeeded in synthesizing an optically active 4-hydroxy-3-methyl-2-2'-propynyl-2-cyclopentenone acid phthalate. Further, the inventors developed a method for producing an optically active (+)-(s)-4-hydroxy-3-methyl-2-2'-propynyl-2-cyclopentenone, an unknown compound before the present invention, by hydrolyzing the optically active acid phthalate in water or a solvent containing water with a base of a small excess over the theoretical equivalent.

And, the inventors developed a method for producing novel (±)-4-hydroxy-3-methyl-2-2'-propynyl-2-cyclopentenone acid phthalate, which is the starting material of the above process.

The method of the present invention is carried out as follows: Firstly, the (±)-α-phenyl-β-p-tolylethylamine salt of (−)-4-hydroxy-3-methyl-2-2'-propynyl-2-cyclopentenone acid phthalate is obtained by reacting 1 mole of (±)-4-hydroxy-3-methyl-2-2'-propynyl-2-cyclopentenone acid phthalate which may optionally contain in part an optically active 4-hydroxy-3-methyl-2-2'-propynyl-2-cyclopentenone acid phthalate with 0.5 to 1.0 mole of an optically active (+)-α-phenyl-β-p-tolylethylamine in an inert solvent, collecting the precipitated crystalline salt by filtration and if necessary recrystallizing the salt from a suitable solvent. Then, the objective optically active (+)-(s)-4-hydroxy-3-methyl-2-2'-propynyl-2-cyclopentenone is obtained by decomposing the salt as usual with an acid or alkali to obtain (−)-4-hydroxy-3-methyl-2-2'-propynyl-2-cyclopentenone acid phthalate and hydrolyzing the acid phthalate in water or a solvent containing water with a base below the small excess of the theoretical equivalent.

Referring to the present invention in more detail, 1 mole of (±)-4-hydroxy-3-methyl-2-2'-propynyl-2-cyclopentenone acid phthalate which may optionally contain in part an optically active 4-hydroxy-3-methyl-2-2'-propynyl-2-cyclopentenone acid phthalate is allowed to react with 0.5 to 1.0 mole of an optically active (+)-α-phenyl-β-p-tolylethylamine in an inert solvent (e.g. aromatic hydrocarbon solvents such as benzene and toluene; ether solvents such as diethyl ether and diisopropyl ether; aliphatic hydrocarbon solvents such as n-hexane, n-pentane and n-heptane; mixtures of these solvents in suitable proportions).

The reaction is effected usually at temperature of −10° C. to the boiling point of the used solvent and comes to an end in 10 minutes to 48 hours. The precipitated crystalline salt is collected by filtration and if necessary recrystallized from a suitable solvent (e.g. aromatic hydrocarbon solvents such as benzene and toluene; ether solvents such as diethyl ether and diisopropyl ether; aliphatic hydrocarbon solvents such as n-hexane, n-pentane and n-heptane; alcohol solvents such as isopropyl alcohol, ethyl alcohol and tert-butyl alcohol; mixtures of these solvents in suitable proportions) to obtain the (+)-α-phenyl-β-p-tolylethylamine salt of (−)-4-hydroxy-3-methyl-2-2'-propynyl-2-cyclopentenone acid phthalate. This salt is then decomposed as usual with an acid or alkali to obtain (−)-4-hydroxy-3-methyl-2-2'-propynyl-2-cyclopentenone acid phthalate. Examples of the used acid includes diluted hydrochloric acid and diluted sulfuric acid, and examples of the used alkali are the aqueous solution of hydroxides of an alkali metal (e.g. sodium, potassium) and carbonates of an alkali metal (e.g. sodium, potassium). The (−)-acid phthalate is then decomposed at room temperature (10° C.) to 200° C. for 5 minutes to 100 hours in water or a solvent containing water. In this case, the application of pressure, 1.5 to 10 atm., to the reaction system for rapid completion of the reaction, the addition of a base of a 0 to 1.5 moles of the theoretical equivalent based on (−)-4-hydroxy-3-methyl-2-2'-propynyl-2-cyclopentenone acid phthalate and the addition of a pH buffer (e.g. an aqueous solution of sodium acetate, sodium hydrogen phosphate, sodium dihydrogen phosphate, potassium hydrogen phosphate, potassium dihydrogen phosphate, etc.) give desirable effects in terms of the rate of reaction. The usable solvent includes for example water and water-soluble solvents (e.g. methanol, ethanol, glycerin, ethylene glycol, tetrahydrofuran, acetone, dioxane, dimethylformamide, dimethyl sulfoxide). Also, in order to protect (+)-4-hydroxy-3-methyl-2-2'-propynyl-2-cyclopentenone produced during the reaction, a solvent sparingly soluble in water (e.g. diethyl ether, benzene, toluene, chloroform, carbon tetrachloride, n-hexane, methyl ethyl ketone) may be added to the reaction system, or the reaction may be carried out in a buffer solution to keep the pH of the reaction system nearly neutral. The base used herein is not particularly limited, and it includes for example hydroxides and oxides of an alkali metal (e.g. sodium, potassium) or alkaline earth metal (e.g. calcium, barium), their salts with weak acids (e.g. carbonic acid, bicarbonic acid, boric acid, acetic acid), ammonia and organic amines. As the organic amines, any of primary, secondary and tertiary amines may be used. For example, there may be given ethylamine, triethylamine, cyclohexylamine, dicyclohexylamine, pyridine, pyrrolidine, piperidine, aniline, quinoline and picoline. The reaction solution thus obtained is then saturated with sodium chloride, followed by extraction. The organic layer separated is washed with a sodium chloride-saturated water, dried and concentrated under reduced pressure to obtain almost pure (+)-4-hydroxy-3-methyl-2-2'-propynyl-2-cyclopentenone.

Next, there is provided a method for producing (±)-4-hydroxy-3-methyl-2-2'-propynyl-2-cyclopentenone acid phthalate of the formula (II).

Firstly, (±)-4-hydroxy-3-methyl-2-2'-propynyl-2-cyclopentenone acid phthalate is obtained by reacting (±)-4-hydroxy-3-methyl-2-2'-propynyl-2-cyclopentenone with phthalic anhydride in the presence of a base in an inert solvent, adding water in an amount of 0.5 to 3.0 times the volume of the reaction solution and separating the water layer, adding a small amount of 10% aqueous hydrochloric acid to the obtained water layer for neutralization, extracting with an organic solvent such as ethyl acetate, diethylether, etc., and removing the organic solvent by evaporation. The resulting oily product, (±)-4-hydroxy-3-methyl-2-2'-propynyl-2-cyclopentenone acid phthalate is obtained.

Referring to the present invention in more detail, the reaction is effected usually at a temperature of 0° to the boiling point of the used solvent and comes to an end in 5 minutes to 10 hours.

The reaction may be carried out in an organic solvent (e.g. aromatic hydrocarbon solvents such as benzene and toluene; ether solvents such as diethyl ether and diisopropyl ether; dichloromethane. Examples of the base includes tertiary amines such as pyridine and triethylamine. The base is usually employed in an amount of 1.0 to 2.0 moles to 1 mole of (±)-4-hydroxy-3-methyl-2-2'-propynyl-2-cyclopentenone. Phthalic anhydride is usually employed in an amount of 1.0 to 1.5 moles to 1 mole of (±)-4-hydroxy-3-methyl-2-2'-propynyl-2-cyclopentenone. The present invention will be illustrated in more detail with reference to the following examples.

EXAMPLE 1

(±)-4-Hydroxy-3-methyl-2-2'-propynyl-2-cyclopentenone acid phthalate (8.9 g) was dissolved in diethyl ether (30 ml), and (+)-α-phenyl-β-p-tolylethylamine (6.3 g) was added thereto, followed by stirring at room temperature for a whole day and night. The produced salt is collected by filtration and washed with diethyl ether to obtain 15.0 g of the salt as white crystals (m.p. 96° C.). Benzene (150 ml) was added to this salt, and the mixture was heated to 70° C. and allowed to cool with stirring for a whole day and night. The produced crystals were collected by filtration to obtain 6.3 g of a white crystal (m.p. 112° C.). The crystal was then recrystallized from benzene (50 ml) to obtain 5.4 g of a white crystals (m.p. 112° C.). The crystal was then recrystallized from benzene (50 ml) to obtain 5.4 g of a white crystal (m.p. 115° C.). The crystal was then suspended in diethyl ether (90 ml), and a 1% aqueous hydrochloric acid (75 ml) was added, followed by stirring for 30 minutes. The ether layer was once washed with a 1% aqueous hydrochloric acid, and the solvent was removed by evaporation to obtain 2.7 g of (−)-4-hydroxy-3-methyl-2-2'-propynyl-2-cyclopentenone acid phthalate as an oily product. $[\alpha]_D^{22} = -21.5°$ (c=0.53, CHCl$_3$). This oily product was once dissolved in a mixture of water (18 ml) and sodium hydrogen carbonate (0.75 g), and then a 10% aqueous hydrochloric acid (2–3 cc) was added to the solution to adjust the pH to 5. The solution was refluxed with stirring for 8 hours. The reaction solution was cooled and extracted with addition of ethyl acetate, water and sodium chloride. After removing the solvent by evaporation, the resulting crude oily product was purified by passing it through a silica gel column using a 2:1 mixture of n-hexane and ethyl acetate as solvent. Thus, 1.1 g of (+)-4-hydroxy-3-methyl-2-2'-propynyl-2-cyclopentenone was obtained. $[\alpha]_D^{21} = +22.4°$ (c=0.5, CHCl$_3$), $n_D^{23.5}$ 1.5275. By gas chromatography on an optically active column, it was found that the optical purity of this product was 100%.

EXAMPLE 2

(−)-4-Hydroxy-3-methyl-2-2'-propynyl-2-cyclopentenone acid phthalate was synthesized by the same manner as in the Example 1. $[\alpha]_D^{22} = -21.5°$ (c=0.53, CHCl$_3$). The oily (−)-acid phthalate (2.7 g) was dissolved in water (25 ml) and the mixture was refluxed with stirring for 10 hours. The reaction mixture was worked up and purified in the same manner as in Example 1. Thus, 0.9 g of (+)-4-hydroxy-3-methyl-2-2'-propynyl-2-cyclopentenone was obtained. $[\alpha]_D^{20} = +21.8°$ (c=0.4, CHCl$_3$), $n_D^{20}$ 1.5270.

EXAMPLE 3

(−)-4-Hydroxy-3-methyl-2-2'-propynyl-2-cyclopentenone acid phthalate ($[\alpha]_D^{22}=21.0°$ (c=0.50, CHCl$_3$)) (2.7 g) was dissolved in water (20 ml) solution of sodium acetate (0.5 g) and the resulting solution was refluxed with stirring for 15 hours. 0.85 Gram of (+)-4-hydroxy-3-methyl-2-2'-propynyl-cyclopentenone was obtained after the same purification as in Example 1. $[\alpha]_D^{20} = +20.8$ (c=0.51, CHCl$_3$).

EXAMPLE 4

(±)-4-Hydroxy-3-methyl-2-2'-propynyl-2-cyclopentenone (7.50 g) and phthalic anhydride (7.40 g) were dissolved in toluene (50 ml). Triethylamine (6.0 g) was added to this solution over an hour. The resulting solution was stirred for 2 hours at 25° C. Then water (50 ml) was added to the mixture and the water layer was separated. 10% Hydrochloric acid (about 25 ml) was added to the water layer and this solution was twice extracted with diethyl ether (100 ml×2). The ether extract was washed with NaCl solution (50 ml) and dried over MgSO$_4$. After removing the solvent, the almost pure (±)-4-hydroxy-3-methyl-2-2'-propynyl-2-cyclopentenone acid phthalate (13.2 g) was obtained. Yield: 88.6%, $n_D^{25.5}$ 1.5403.

EXAMPLE 5

The optically active (−)-(s)-2-methyl-3-2'-propynyl-cyclopent-2-en-4-on-1-yl 2,2,3,3-tetramethylcyclopropanecarboxylate [$\alpha_D = -7.2°$, c=(0.5, CHCl$_3$)] [Compound A] is obtained by reacting the present compound, (+)-(s)-4-hydroxy-3-methyl-2-2'-propynyl-2-cyclopentenone with 2,2,3,3-tetramethylcyclopropanecarbonyl chloride in the manner described in U.S. Pat. No. 3,876,681.

And, the Compound A and reference compound were dissolved in kerosene to obtain an oil spray having the prescribed concentration of each compound. Ten northern house mosquito female adults (*Culex pipiens pallens*) and ten housefly adults (*Musca domestica*) were liberated in a (70 cm)$^3$ glass chamber, and 0.7 ml of the above oil spray was sprayed into the chamber. Thereafter, the number of knocked-down insects was counted with the lapse of time, and the value of KT$_{50}$ was obtained from the average knock-down ratio of three replications according to the Finney's method.

| Test compound | Concentration (%) | KT$_{50}$ (sec) | |
| --- | --- | --- | --- |
| | | Housefly adult | Northern house mosquito female adult |
| Compound A | 0.1 | 84 | <30 |
| | 0.05 | 130 | 38 |
| | 0.025 | 200 | 68 |
| Reference Compound* | 0.1 | 120 | 44 |
| | 0.05 | 210 | 85 |
| | 0.025 | 380 | 122 |

*Compound described in U.S. Pat. No. 3876681.

What is claimed is:
1. (+)-(s)-4-Hydroxy-3-methyl-2-2'-propynyl-2-cyclopentenone.

* * * * *